United States Patent [19]
MacGregor et al.

[11] Patent Number: 5,907,032
[45] Date of Patent: May 25, 1999

[54] THROMBIN PREPARATION

[75] Inventors: Ian Randle MacGregor; John Charles Hardy, both of Edinburgh; Olive Drummond, Oue, all of United Kingdom

[73] Assignee: Common Services Agency, Edinburgh, United Kingdom

[21] Appl. No.: 08/913,162

[22] PCT Filed: Feb. 23, 1996

[86] PCT No.: PCT/GB96/00423

§ 371 Date: Nov. 20, 1997

§ 102(e) Date: Nov. 20, 1997

[87] PCT Pub. No.: WO96/26269

PCT Pub. Date: Aug. 29, 1996

[30] Foreign Application Priority Data

Feb. 24, 1995 [GB] United Kingdom ................... 9503750

[51] Int. Cl.⁶ ................ A61K 35/14; A23J 1/00
[52] U.S. Cl. ............. 530/384; 530/380; 530/381; 530/383; 530/412; 530/416; 530/417; 530/422; 530/427; 424/529; 424/530
[58] Field of Search ................. 530/384, 380, 530/381, 383, 412, 416, 417, 422, 427; 424/529, 530

[56] References Cited

U.S. PATENT DOCUMENTS

| | | | |
|---|---|---|---|
| 5,143,838 | 9/1992 | Kraus et al. | 435/214 |
| 5,151,499 | 9/1992 | Kameyama et al. | 530/381 |
| 5,219,995 | 6/1993 | Herring et al. | 530/381 |
| 5,304,372 | 4/1994 | Michalski et al. | 424/94.64 |

FOREIGN PATENT DOCUMENTS

| | | |
|---|---|---|
| 0 378 798A1 | 12/1989 | European Pat. Off. . |
| 0 378 208A3 | 1/1990 | European Pat. Off. . |
| 0 528 701A1 | 7/1992 | European Pat. Off. . |
| 0 541 507A3 | 11/1992 | European Pat. Off. . |

OTHER PUBLICATIONS

Sigma Chemical Co.: "Biochemicalien organische verbindingen voor research en diagnostica" 1994, Sigma Chemi, Bornem, Belgie, XP002004367; pp. 982–983.

Godwin et al, *Biochem. Biophys. Res. Comm.*, vol. 202, No. 1, pp. 321–327, Jul. 15, 1994.

Moyer et al, *Arterioscler. Thromb. Vasc. Biol.*, vol. 18, pp. 458–465, 1998.

*Primary Examiner*—Cecilia J. Tsang
*Assistant Examiner*—Abdel A. Mohamed
*Attorney, Agent, or Firm*—Myers Bigel Sibley & Sajovec

[57] ABSTRACT

A process for preparing thrombin which comprises treating a mixture comprising prothrombin, factor Xa, factor Va, and phospholipids with calcium ions, at a pH of 6.0–7.0 is provided. In particular the pH of 6.0–7.0 may be generated by the addition of the calcium ions or by buffering the preparation to a pH of 6.0–7.0. Thrombin preparations so produced may be subjected to further purification and are particularly stable even when substantially free of exogenous stabilizing agents such as proteins, sugars, polyol and mixtures thereof, and may be subject to freeze-drying and a virus inactivation by heat treatment.

23 Claims, 2 Drawing Sheets

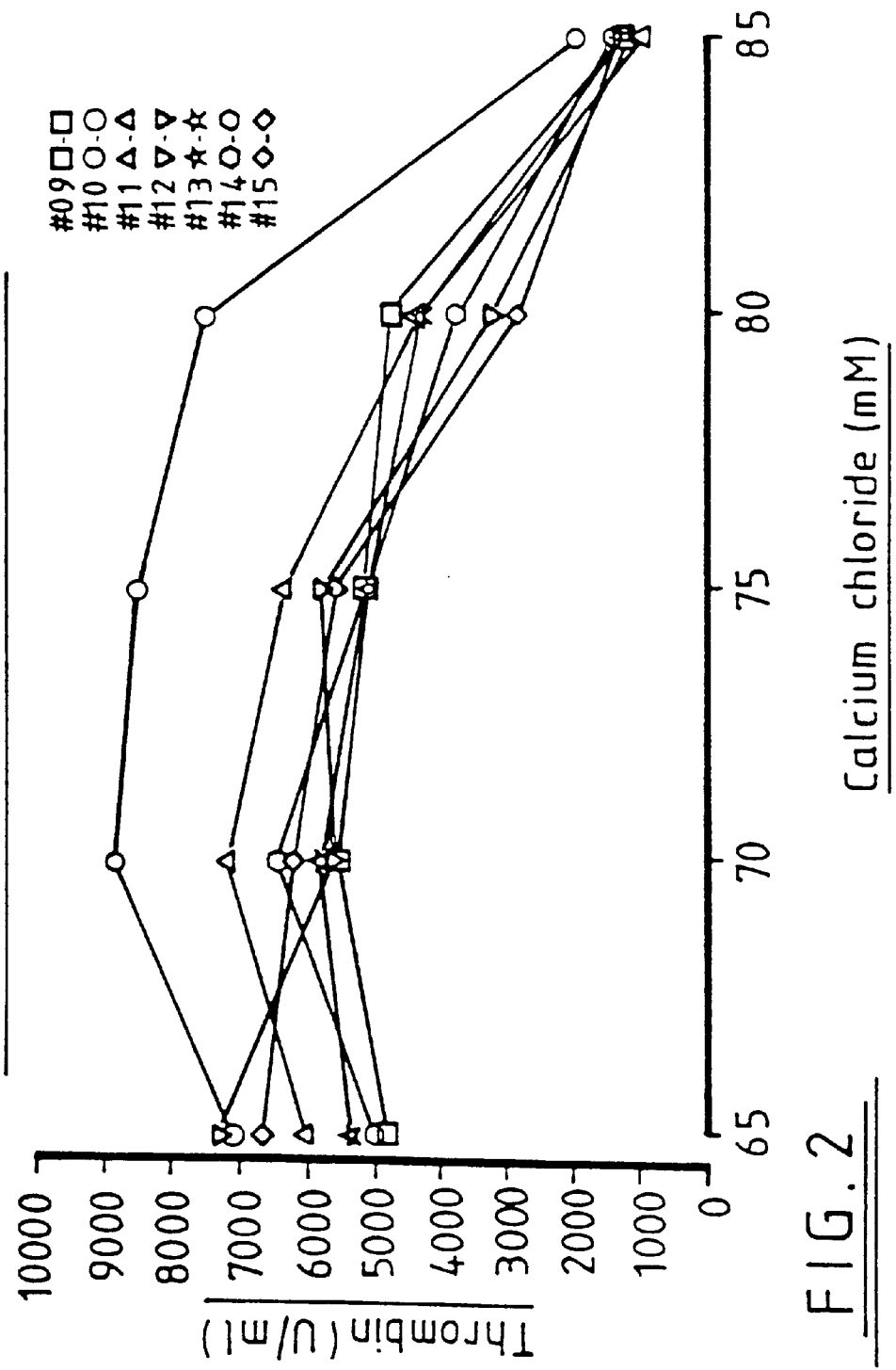

THROMBIN PREPARATION

FIELD OF THE INVENTION

The present invention relates to a novel process for the production of thrombin particularly human thrombin and to thrombin preparations capable of being produced in a freeze dried form, which may be heat-treated in order to inactivate any viruses present.

BACKGROUND OF THE INVENTION

Thrombin is the product of the activation of prothrombin by Factor Xa in plasma. It is a potent broadly specific serine proteinase that converts fibrinogen to fibrin and promotes fibrin cross-linking by activating Factor XIII. Amongst a number of other observed biological activities, thrombin also controls several feedback loops in the clotting cascade and induces the platelet release reaction (1, 2).

Thrombin has been used as a topical haemostatic agent for many years. However, it is as a component of fibrin sealant (fibrin glue) that the clinical use of thrombin is likely to expand. Thrombin is used in fibrin sealant to convert fibrinogen to fibrin on a cut surface or within a graft and numerous surgical applications have been described in a wide range of surgical specialties (3, 4).

Bovine thrombin is currently used widely as a topical haemostatic agent or as a component of commercial fibrin sealant products. While such thrombin products are biologically effective, they are associated with well-documented risk of allergic responses and induction of antibodies to the bovine thrombin or to impurities such as bovine factor V, usually after repeat use (5, 6 and 7). Ortel et al (8) recently concluded that such acquired coagulation factor inhibitors probably occur more commonly than is currently appreciated and although frequently clinically benign, these inhibitors may be associated with life-threatening haemorrhage. For this reason the development of a process to produce human thrombin suitable for use as a topical haemostat or for inclusion in a fibrin sealant product, has been sought.

Intrinsically, thrombin is formed when prothrombin (Factor II) is converted by activated Factor X, activated a Factor V, phospholipid and calcium ions into thrombin. Conversion of prothrombin to thrombin can occur without some of the associated components, however, the rate of conversion is undesirably slow.

There are three main in vitro prothrombin conversion methods known in the art. The first method relies on the use of thromboplastin. Prothrombin is converted to thrombin using thromboplastin preferably in the presence of calcium chloride. This is described in a number of patent specifications such as EP 0439156A and EP 0505604A. A disadvantage of this method is that the thromboplastin is usually a crude preparation which has been prepared from freshly homogenised brain, lung or intestinal tissue. This procedure is not appropriate for the preparation of human thrombin as the reagents, depending on their source, can carry the risk of virus or cross-species contamination.

A second method utilises some components of snake venom to yield thrombin (9, 10, 11). However, it has been reported that some of the venoms do not cleave the same bonds within prothrombin, as the natural activator, Factor Xa (12). Thus, there may be dangerous implications should a non-physiological form of thrombin be used clinically.

The third in vitro method is essentially the same as the intrinsic in vivo process, wherein prothrombin is converted to thrombin by activated Factor X, Factor V, phospholipid and calcium ions under near physiological conditions. This has been described, for instance in, EP 0528701, EP 0378798 and U.S. Pat. No. 5,219,995. However, the thrombin produced is often unstable unless exogenous proteins, polyols and/or sugars are added to the thrombin to stabilise it.

Since human thrombin is derived from plasma obtained from blood donations, there is a risk of contamination of the thrombin by any viruses present in the original blood donation. Thus, any human thrombin preparation designed for clinical use, should be subjected to a virus inactivation step, prior to use.

Virus-inactivation by solvent-detergent treatment has been described previously (13). However, the thrombin preparation may need to be subjected to further purification steps in order to remove the solvent-detergent. Other workers have described the use of virus/inactivated prothrombin feedstocks, but have not described methods for virus/inactivation of the thrombin products prepared from them, for example EP 0378798 and EP 0543178. Terminal (e.g. a final step of a process) viral-inactivation of the product is viewed as probably the safest and most effective method of virus/inactivation, as it minimises the chance of recontamination.

There is thus a requirement in the art to produce thrombin which is terminally virus/inactivated, especially by heat-treatment.

Generally speaking the present invention is based on the surprising discovery that prothrombin can be converted to thrombin in good yield, under acidic conditions and that these acidic conditions promote the stability of the thrombin generated.

SUMMARY OF THE INVENTION

More specifically, a first aspect of the present invention provides a process for preparing thrombin which comprises treating a mixture comprising prothrombin, Factor Xa, Factor Va and phospholipids with calcium ions at a pH less than pH 7.0.

Generally, the mixture comprising prothrombin, Factor Xa, Factor Va and phospholipids may be obtained from a supernatant of a cryoprecipitate (which is formed by freezing and thawing plasma) of human plasma. The mixture may be obtained by chromatographic purification of the supernatant of cryoprecipitated plasma, generally by anion-exchange chromatography. More particularly a DEAE-cellulose eluate of absorbed supernatant of cryoprecipitated plasma, which may be used for the production of clinical Factor IX concentrates, can serve as the mixture for thrombin production (14). The mixture may comprise additional clotting factors, such as, Factor X, Factor V, Factor IX, Factor IXa and trace amounts of thrombin.

The prior art (e.g. EP 0378789 and EP 0528701) has previously taught the addition of low levels of calcium ions (5–25 mM) to a mixture comprising prothrombin, at or around physiological conditions (pH 7.0–7.3) and EP 0528701 describes that the addition of higher levels of $CaCl_2$ inhibits the preparation of thrombin. It might be expected that conversion of prothrombin to thrombin would proceed best in conditions which approach those of physiological conditions. It is thus a surprising feature of the present invention that thrombin may be prepared in particularly good yield at a pH of less than pH 7.0. Preferably the pH is between pH 6.0–7.0 and more preferably between pH 6.4–6.6. Without wishing to be restricted to any postulated theories, it is thought that the pH of less than pH 7.0 limits autodegradation of thrombin produced.

Generally the pH of less than pH 7.0 may be generated by the addition of $Ca^{2+}$ ions, (in particular $CaCl_2$) at concentrations of 50 mM–90 mM, more preferably 60 mM–80 mM and most preferably 65 mM–75 mM, to the mixture.

Addition of $CaCl_2$ in the ranges specified, further generally results in a drop in the pH of the mixture which may be sufficient to reach the required pH.

Alternatively, the mixture may be buffered to between pH 6.0–7.0 or more preferably between pH 6.4–6.6 by any suitable buffer known to buffer in the required range, before adding $Ca^{2+}$ ions to initiate the conversion of prothrombin to thrombin. Examples of suitable buffers include MES (2-[N-Morpholino]ethanesulphonic acid); ACES (2-[2-Amino-2-oxoethyl)amino]ethanesolphonic acid); BES (N,N-bis[2-Hydroxyethyl]-2-aminoethanesulphonic acid); MOPS (3-[N-Morpholino]propanesulphonic acid); TES (N-tris[Hydroxymethy]methyl-2-aminoethanesulphonic acid) and HEPES (N-[2-Hydroyethyl]piperazine-N-[2-ethanesulphonic acid) and the like.

In order to convert substantially all the prothrombin to thrombin, the conversion should proceed for a period of time and at a suitable temperature to effect conversion. Typically the conversion should be allowed to proceed for 12–24 hours and more preferably for 16–20 hours. The conversion may proceed at room temperature, typically between 18–25° C. and does not require incubation at higher temperatures.

Generally thrombin prepared in this manner has a thrombin clotting activity of between 4,000–9,000 U/ml and a specific activity of between 250–700 U/mg. This is considerably higher than the activity of the thrombin prepared by the process described in EP 0528701 (clotting activity 700–1,000 U/ml and a specific activity of 20–40 U/mg).

Some unwanted insoluble material may be found in the thrombin preparation probably due to the generation of fibrin by the action of generated thrombin on any fibrinogen present as a contaminant in the original DEAE-cellulose eluate and of insoluble calcium phosphate. The unwanted insoluble material may be removed by centrifugation or by a filtering process. However, in some instances, the preparation is too viscous and so the thrombin preparation is preferably diluted to reduce the viscosity. A dilution of 1 volume of thrombin preparation with up to 3 volumes buffer, for example 3 volumes which can be any buffer suitable for use in the range of pH 6.0–7.0, is generally carried out. Typical buffers include 40 mM sodium gluconate or 20 mM MES, both at pH 6.5. The diluted preparation may then be centrifuged or filtered to remove any insoluble material. Alternatively 20 mM citrate, pH 6.5 may be used as the diluting buffer. This may remove the need for centrifugation or filtering, possibly due to the solubilisation of insoluble calcium phosphate.

The diluted thrombin preparation is suitable for immediate further processing, or may be stored at −40° C. for at least six months without substantial loss of clotting activity. Alternatively, the diluted material may be formulated and freeze-dried as an intermediate purity preparation.

A specific activity of the thrombin preparation of between 250 U/mg to 700 U/mg is equivalent to a thrombin purity of between about 6%–17.5% based on a comparison to a specific activity of pure α-thrombin of 4,000 U/mg. While this is sufficient in most clinical instances, it is possible to subject the thrombin preparation to further processing to yield a thrombin of higher purity.

Further processing may comprise chromatographic purification of thrombin with an optional solvent/detergent virus inactivation step prior to chromatographic purification. A suitable solvent/detergent virus/inactivation step has been previously described in Edwards et al (13).

Chromatographic purification is generally carried out by cation-exchange chromatography. Typically cation-exchange resins which may be employed include MONO-S (TRADEMARK), S-SEPHAROSE FF (TRADEMARK) and S-SEPHAROSE BIG BEADS (TRADEMARK), all methyl sulphonate strong cation-exchangers produced by Pharmacia Biotech, although other sulphonate gels or other cation-exchangers may be employed. The chromatography step serves to remove solvent and detergent, if a solvent/detergent virus inactivation step has been carried out and also serves to purify the thrombin preparation.

Typically the thrombin preparation is bound to the cation-exchange chromatography resin and a purified thrombin is eluted using a suitable buffer with increased salt concentration. Examples of suitable buffers include 20 mM citrate pH 6.5, 20 mM MES pH 6.5 and 40 mM gluconic acid pH 6.5. The pH of the buffer should preferably be in the range of pH 6.0–7.0 and more preferably pH 6.4–6.6 in order to preserve the activity of the purified thrombin. Usually several salts are suitable for eluting with any given cation-exchange resin and typically these include NaCl.

The concentration of eluted purified thrombin depends directly upon the amount bound to the resin, but typically concentrations of purified thrombin between 4,000–9,000 U/ml may be obtained. Even the lower range of these concentrations is adequate to allow suitable dilution with a formulation buffer, for subsequent freeze-drying.

Purified thrombin may be frozen directly in elution buffer and stored for up to six months without substantial loss of thrombin activity. However, for ease of storage it is desirable that the intermediate purity thrombin and purified thrombin, be freeze-dried.

Freeze-drying often results in a loss in activity of thrombin (intermediate purity thrombin and purified thrombin) and it is thus important to formulate the thrombin with a formulation buffer. This formulation buffer helps stabilise the thrombin during freeze-drying. Prior to formulating the thrombin, it is often desirable to centrifuge and/or filter the thrombin to remove insoluble material.

The art has previously described that the addition of stabilising agents such as polyols, for instance, glycerol, mannitol and sorbitol; sugars such as sucrose and glucose and/or exogenous proteins such as albumin, to a thrombin preparation is desirable to improve the stability of a thrombin preparation, especially during freeze-drying. It is thus a surprising feature of the present invention that thrombin may be prepared, which is substantially stable without additional stabilising agents such as polyol, sugar, protein and mixtures thereof.

Thus, in a further aspect the present invention provides a thrombin preparation, the preparation comprising thrombin substantially free of exogenous stabilising agents (such as protein, sugar, polyol and mixtures thereof) buffered at a pH of less than pH 7.0.

Generally the thrombin preparation is freeze-dried and optionally heat-treated. Thus, in a still further aspect, the present invention provides a freeze-dried, optionally heat-treated, thrombin preparation, substantially free of exogenous stabilising agents, such as protein, sugar or polyol and mixtures thereof.

Preferably the thrombin preparation is buffered to between pH 6.0–7.0, more preferably pH 6.4–6.6. This may be achieved by for instance 40 mM gluconic acid or 20 mM MES buffer in the suitable pH range. Preferably, the thrombin preparation further comprises citrate at a concentration of 10 mM–30 mM, typically sodium citrate. More preferably the preparation further comprises sodium chloride at a concentration of between 100–250 mM for example 100–200 mM. A thrombin preparation comprising citrate and sodium chloride in addition to gluconate or MES has been found to be most stable to freeze-drying and optional heat-treatment. That is, the thrombin preparation retains a greatest percentage of clotting activity after freeze-drying and optional heat-treating.

Freeze-drying is preferably carried out employing a two-stage freezing procedure. The frozen product is then primary dried at a shelf temperature of –20° to –30° C. and then secondary dried at a shelf temperature of +15° to +30° C.

The freeze-dried thrombin preparation may then be heat-treated in order to inactivate any virus contaminants. Typically dry heat-treatment is carried out at temperatures of between 70° C. to 100° C. for up to 96 hours. A particularly preferred heat-treatment is approximately 80° C. for around 72 hours.

DETAILED DESCRIPTION OF PREFERRED EMBODIMENTS

Embodiments of the present invention will now be described by way of Example, with reference to the attached Figures.

BRIEF DESCRIPTION OF THE FIGURES

FIG. 2 shows the amount of thrombin in U/ml generated over a range of added calcium ion concentrations, in accordance with an embodiment of the present invention.

EXAMPLES SECTION

Example 1

Figure 1:
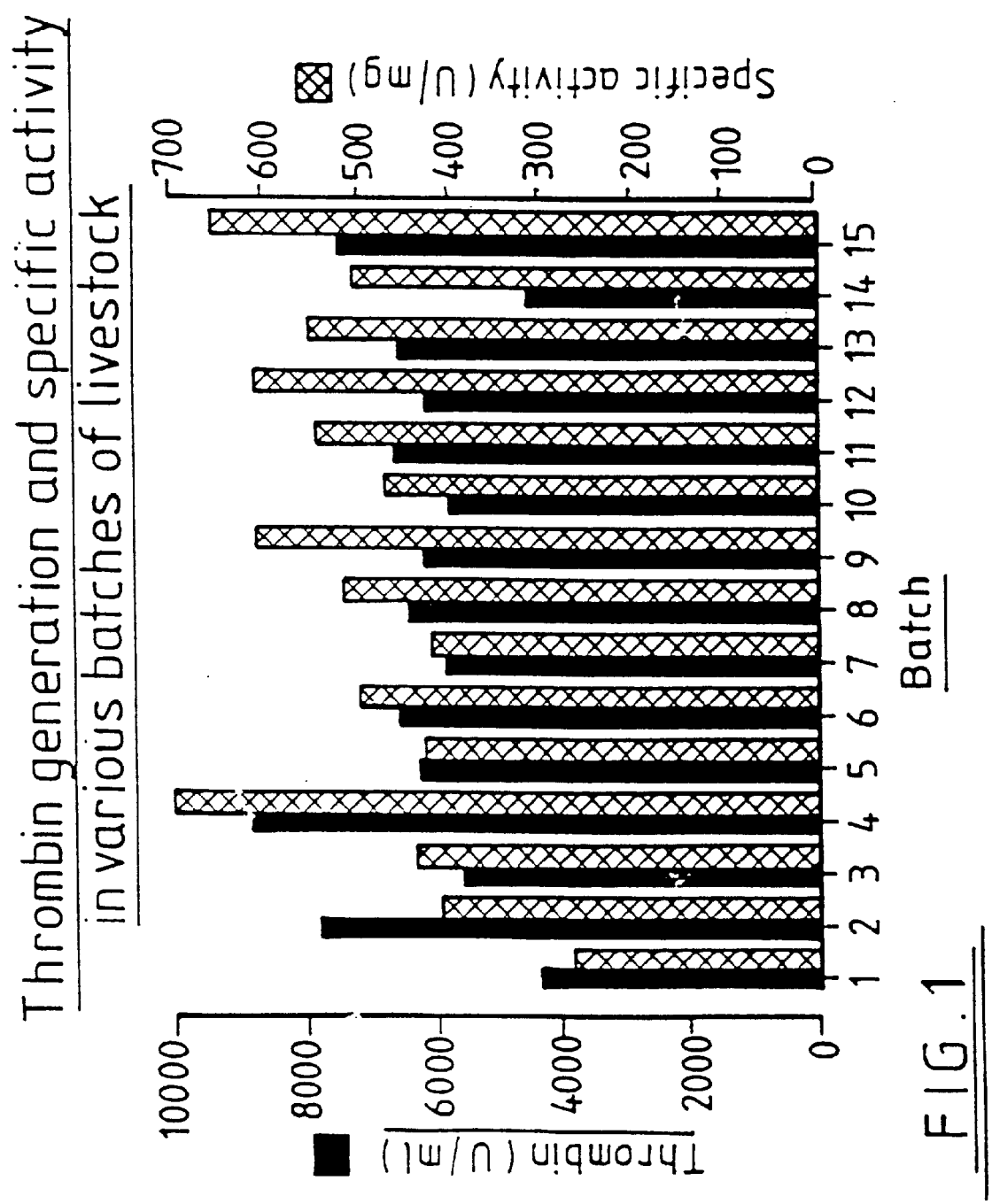
FIG. 1 shows the thrombin clotting activity in U/ml and specific activity in U/mg of 15 separate batches of thrombin prepared in accordance with one embodiment of the present invention.

Preparation of a mixture comprising prothrombin, Factor Xa, Factor Va and phospholipid by DEAE-cellulose 450 liters of cryoprecipitate plasma was adjusted to pH 6.9±0.05 and diluted with 150 liters of pyrogen free $H_2O$ to a final volume of 600 liters. 6 kg of DEAE-cellulose gel (DE-52 Whatman) was then added to the plasma/water solution and the resulting suspension mixed continuously for one hour to bind the clotting factors to the gel. The gel was then collected by centrifugation and the supernatant discarded. The gel was then resuspended in 30 mM citrate, 30 mM phosphate pH 6.9 buffer and the resulting suspension was poured into a chromatography column. The column was then packed by washing with 21 liters of the same buffer. The clotting Factors were then eluted from the column with an elution buffer of 30 mM citrate, 30 mM phosphate, 200 mM NaCl, pH 6.9. The eluate pool (3.1 liters) was then filtered (0.45 μm pore size) into sterile bottles and frozen.

The eluate pool contains substantial amounts of prothrombin (Factor II) (at 80 μM and about 25% of the total protein). It also includes factors IX and X, activated and non-activated (at about 5 μM), coagulant-active phospholipid and sufficient trace amounts of Factors V and VIII to support the physiological conversion of prothrombin to thrombin via the intrinsic clotting pathway.

Example 2

Preparation of intermediate purity thrombin

Frozen DEAE-cellulose eluate (prepared according to Example 1) was thawed at room temperature or in a 37° C. water bath. (Typical values of the eluate were as follows: conductivity=17 mS; pH=7.0; 30 mM citrate; 30 mM phosphate; 200 mM sodium; 200 mM chloride; 15 mg/ml total protein and prothrombin 60 U/ml).

1M $CaCl_2$ solution was then added dropwise to the thawed eluate, with stirring, at a ratio of 75 ml $CaCl_2$ to 1,000 ml eluate, at 20° C. This resulted in a final calcium concentration of 70 mM and a drop in pH in the mixture to pH 6.4–6.6. The reaction was allowed to proceed with stirring overnight for 18 hours at 20° C., to convert the prothrombin to thrombin.

In 15 experiments, the thrombin clotting activity was 6,333±1,146 U/ml (mean±SD) and specific activity of 508±110 U/mg (see FIG. 1). SDS PAGE indicated that effectively all the prothrombin band was converted into bands co-migrating with thrombin, by the end of the activation period.

Thrombin clotting activity was measured by fibrinogen clotting time at room temperature with visual detection and duplicate samples. To 200 μl of human fibrinogen solution at 5 mg/ml in 50 mM tris-HCl 100 mM NaCl pH 7.5 was added 100 μl of standard (1–4 U/ml) or test solutions of thrombin diluted in 50 mM tris-HCl, 100 mM NaCl pH 7.5 supplemented with 100 mM $CaCl_2$ and 0.1% w/v bovine serum albumin, whereupon time to subsequent clot formation was recorded. A standard curve was constructed by plotting $log_{10}$ thrombin concentration (U/ml) against $log_{10}$ clotting time (sec) using bovine thrombin standardised against the human alpha-thrombin standard 89/588. Thrombin clotting activity of test samples was derived by extrapolation from the standard curve (15).

Example 3

Effect of varying the pH of the reaction solution during activation

Following the procedure described in Example 1, resulted in a mixture with a pH of 7.0–7.2. This immediately decreased to pH 6.5 on addition of $CaCl_2$ to 70 mM. There was then a steady decrease in pH to 6.1–6.3 during the conversion period (18 hours). The fall in pH was a requirement for the successful generation of thrombin of high activity. This was demonstrated by comparative experiments, where the pH of the solution was adjusted to pH 7.0 or pH 7.5 immediately after the addition of $CaCl_2$. Here the final pH values at the end of the reaction period were pH 6.7 and pH 7.1 respectively and a much lower amount of thrombin activity was generated (see Table 1).

TABLE 1

| Example | pH of the mixture, immediately after $CaCl_2$ addition (adjusted as necessary) | pH of the mixture at the end of the conversion period (18 hours) | Clotting activity (IU/ml) |
| --- | --- | --- | --- |
| 1 | 6.5 | 6.1 | 5716 |
| 2 | 7.0 | 6.7 | 2012 |
| 3 | 7.5 | 7.1 | 1493 |

In a further experiment, the mixture was buffered (20 mM MES) to pH 6.5 immediately after $CaCl_2$ addition. This resulted in an additional small increase in conversion to thrombin, but the-increase in clotting activity was insignificant.

Example 4
Effects of varying the length of time or temperature employed for conversion of prothrombin to thrombin Studies were carried out to determine the optimum time course for the conversion of prothrombin to thrombin. A comparison of the amount of thrombin generated at 16 and 24 hours indicated that a plateau had been reached by 16 hours.

An investigation was also carried out to determine the effect of incubation at 37° C. for one hour prior to subsequent room temperature incubation, in view of a report that this step was necessary to obtain useful yields with this type of feedstock (European Patent Application No. 92401889.8). It was found that while the initial rate of thrombin generation exceeded that obtained at room temperature, the final yield of thrombin was no better at 16 or 24 hours as compared to conversion at room temperature.

Example 5
Effects of varying calcium ion concentration on thrombin production The amount of thrombin generated at 24 hours with a range of added calcium ion concentrations (seven batches of DEAE-cellulose eluates) was determined (FIG. 2). It was found that the addition of 70 mM calcium consistently resulted in efficient conversion of prothrombin to thrombin.

Example 6
Viral inactivation by solvent/detergent

Thrombin prepared according to Example 2 was mixed by stirring with 0.3% tri-(n-butyl) phosphate and a 1% solution of Tween 80 at a temperature of 20°–30° C. for 6 to 24 hours. This was sufficient to inactivate any contaminating lipid-enveloped viruses. The solvent/detergent was removed by chromatography.

Example 7
Chromatographic purification of intermediate purity thrombin

The chromatography step serves to remove solvent and detergent and to purify the intermediate purity thrombin. A 1.6 cm diameter chromatography column was packed with 10 ml of S-SEPHAROSE FF (TRADEMARK) at a linear flow rate of 2.2 cm/min (equivalent to 4.5 ml/min) using 40 mM gluconic acid, 20 mM MES, or 20 mM citrate all at pH 6.5. 100 ml of solvent/detergent treated thrombin according to Example 6 or intermediate purity thrombin according to Example 2, following a 1+3 dilution in equilibrating buffer was filtered at 0.45 μm and applied to the column at the same flow rate. The column was then washed with equilibrating buffer until the absorbency at 280 nm returned to baseline and solvent or detergent were detectable only below acceptable low levels, in the column effluent (typically approximately 150 ml). Thrombin was then eluted from the column by washing with equilibrating buffer containing 0.5M NaCl. Purified thrombin was obtained in about 25 ml at a typical concentration of 4,000 U/ml and 2 mg/ml protein.

The typical yield of purified thrombin after the chromatography step was 88±16%. This yield refers to a thrombin preparation which was not subjected to a solvent/detergent virus inactivation step as described in Example 6.

Example 8
Formulation, freeze-drying and terminal dry heat treatment

Thrombin prepared according to Examples 2 or 6 was centrifuged at 3,000 rpm for 20 minutes at room temperature and then filtered through a Millpore prefilter (AP25) followed by a Whatman 0.2 μm filter (Polydisc AS). The filtered solution was then diluted in a formulation buffer (40 mM gluconic acid or 20 mM MES, 20 mM trisodium citrate, 150 mM NaCl, pH 6.5) to a thrombin activity of 600 U/ml and dispensed in 2 ml lots into glass vials for freeze-drying.

Freeze-drying was performed in a super-Modulyo (Edwards, Crawley) freeze-dryer with a freezing temperature setting of −45° C., followed by a primary drying temperature setting of −25° C. and a secondary drying temperature setting of +20° C.

The vials were then heat-treated to inactivate any contaminating viruses, at 80° C. for 72 hours.

Example 9
Comparison of a stabilising effect on thrombin of various formulation buffers Thrombin was formulated in a variety of formulation buffers, in order to determine the optimum formulation buffer for stabilising thrombin during freeze-drying and subsequent heat-treatment (virus-inactivation).

Intermediate purity thrombin prepared according to Example 2 and purified thrombin prepared according to Example 7, were diluted with various formulation buffers (as described in Table 2) to a thrombin concentration of 600 U/ml. The thrombin preparation was then freeze-dried according to Example 8 and a quantity of the freeze-dried thrombin was also subjected to a heat-treatment of 80° C. for 72 hours. Thrombin clotting activity was determined, as previously described, to determine the percentage clotting activity that remained after freeze-drying and subsequent heat-treatment. The results are shown in Table 2.

It can be seen from Table 2 that formulation buffers comprising 20 mM tris-HCL buffer at pH 7.2 with or without 20 mM trisodium citrate and/or 150 mM sodium chloride, resulted in a recovery of thrombin clotting activity, after freeze-drying, of greater than 74%. However, large losses in activity were seen post-heat-treatment, particularly in the absence of trisodium citrate. The inclusion of sodium chloride in the formulation buffer gave rise to an intact plug of material, whereas without sodium chloride, the plug retracted and collapsed.

Protein (e.g. Human albumin) can also be included in the formulation at concentrations of 0.5 g/l–10 g/l, to act as a bulking agent and improve plug structure and appearance.

When the formulation buffer was made acidic by using gluconic acid or MES buffered at pH 6.5, recovery of thrombin clotting activity after dry heat-treatment was substantially improved.

Long term stability was determined using the gluconic acid buffer formulation (see Table 2). These studies were performed by storing several vials at 4° C. and 37° C., after freeze-drying and heat treatment. No loss in thrombin clotting activity was observed over a six month period, when comparing the 37° C. stored thrombin to the 4° C. stored thrombin.

TABLE 2

| | Recovery of clotting activity (%) | | | |
|---|---|---|---|---|
| | Intermediate purity thrombin | | High purity thrombin | |
| Formulation buffer | Post-FD | Post-HT | Post-FD | Post-HT |
| 20 mM Tris-HCL pH 7.2 | 96 | 12 | 93 | 12 |
| 20 mM Tris-HCL pH 7.2 + 20 mM | 92 | 56 | 91 | 56 |

TABLE 2-continued

Recovery of clotting activity (%)

| Formulation buffer | Intermediate purity thrombin | | High purity thrombin | |
|---|---|---|---|---|
| | Post-FD | Post-HT | Post-FD | Post-HT |
| trisodium citrate 20 mM Tris-HCL pH 7.2 + 150 mM NaCl | 87 | 10 | 74 | 4 |
| 20 mM Tris-HCL pH 7.2 + 20 mM trisodium citrate + 150 mM NaCl | 91 | 41 | 90 | 51 |
| 20 mM gluconic acid + 20 mM trisodium citrate + 150 mM NaCl pH 6.5 | 100 | 99 | 93 | 85 |
| 20 mM MES + 20 mM trisodium citrate + 150 mM NaCl pH 6.5 | nd | 97 | nd | 86 |

FD = Freeze-drying
HT = Heat-treatment of 80° C. for 72 hours in vial
nd = not done

REFERENCES

1. Fenton, J. W. (1981). Thrombin specificity. Ann. N. Y. Acad. Sci. 370:468–495.
2. Suttie, J. W. and C. M. Jackson. (1977). Prothrombin structure activation and biosynthesis. Physiol. Rev. 57:1–65.
3. Brennan, M. (1991). Fibrin Glue. Blood Rev 5:240–244.
4. Gibble, J. W. and P. M. Ness. (1990). Fibrin Glue—The Perfect Operative Sealant. Transfusion 30:741–747.
5. Banninger, H., T. Hardegger, A. Tobler, A. Barth, P. Schupbach, W. Reinhart, B. Lammle, and M. Furlan. (1993). Fibrin Glue in the Surgery—Frequent Development of Inhibitors of Bovine Thrombin and Human Factor-V. Br. J. Haematol. 85:528–532.
6. Berruyer, M., J. Amiral, P. Ffrench, J. Belleville, O. Bastien, J. Clerc, A. Kassir, S. Estanove, and M. Dechavanne. (1993). Immunization by Bovine Thrombin Used with Fibrin Glue During Cardiovascular Operations—Development of Thrombin and Factors-V Inhibitors. J. Thorac. Cardiovasc. Surg. 105:892–897.
7. Rothenberg, D. M. and J. N. Moy. (1993). Anaphylactic Reaction to Topical Bovine Thrombin. Anesthesiology 78:779–782.
8. Ortel, T. L., L. A. Charles, F. G. Keller, P. K. Marcom, H. N. Oldham, W. H. Kane, and B. G. Macik. (1994). Topical Thrombin and Acquired Coagulation Factor Inhibitors—Clinical Spectrum and Laboratory Diagnosis. Am. J. Hematol. 45:128–135.
9. Denson, K. W. E. (1969). Coagulant and anticoagulant action of snake venoms. Toxicon 7:5–11.
10. Ngai, P. K. and J. Y. Change. (1991). A Novel One-Step Purification of Human alpha-Thrombin After Direct Activation of Crude Prothrombin Enriched from Plasma. Biochem. J. 280:805–808.
11. Feldman, P. and L. Winkelman. (1991). Preparation of special plasma products. In Blood Separation and Plasma Fractionation. Wiley-Liss, Inc., 341–383.
12. Rosing, J. and G. Tans (1991). Inventory of exogenous prothrombin activators. Thromb. Haemostats. 65:627–630.
13. Edwards, C. A., M. P. Piet, S. Chin, and B. Horowitz. (1987). Tri(n-butyl) phosphate/detergent treatment of licensed therapeutic and experimental blood derivatives. Vox. Sang. 52:53–59.
14. Middleton, S. M., I. H. Bennett, and J. K. Smith. (1973). A therapeutic concentrate of coagulation factors II, IX and X from citrated, factor VIII-depleted plasma. Vox. Sang. 24:441–456.
15. Gaffney, P. J., A. B. Heath, and J. W. Fenton. (1992). A collaborative study to establish an international standard for alpha-thrombin. Thromb. Haemostats. 67:424–427.

We claim:

1. A process for preparing thrombin which comprises treating a mixture comprising prothrombin, Factor Xa, Factor Va, and phospholipids with calcium ions in the concentration range of 50 mM–90 mM, and having a pH of 6.0 to 7.0.

2. A process for preparing thrombin according to claim 1 wherein the pH is between pH 6.4–6.6.

3. A process for preparing thrombin according to claim 1 wherein the concentration of calcium ions is in the range of 60 mM–80 mM.

4. A process for preparing thrombin according to claim 1 wherein the concentration of calcium ions is in the range of 65 mM–75 mM.

5. A process for preparing thrombin according to claim 1 wherein the concentration of calcium ions result in said pH of 6.0 to 7.0.

6. A process for preparing thrombin according to claim 1 wherein the mixture is buffered to said pH, before adding calcium ions.

7. A process for preparing thrombin according to claim 1 wherein the thrombin is human thrombin.

8. A process for preparing thrombin according to claim 1 wherein the mixture is obtained from a supernatant of a cryoprecipitate of plasma.

9. A process for preparing thrombin according to claim 8 wherein the mixture is obtained by chromatographic purification of the supernatant of cryoprecipitated plasma.

10. A process for preparing a freeze-dried thrombin comprising preparing thrombin according to claim 1 and freeze-drying said thrombin.

11. A process for preparing a freeze-dried thrombin according to claim 10 further comprising heat-treating the freeze-dried thrombin in order to inactivate any viral contaminants.

12. A process for preparing thrombin according to claim 1 further comprising diluting said mixture with up to three volumes of buffer for each volume of said mixture, wherein the buffer is suitable for use in the pH range 6.0 to 7.0.

13. A process for preparing thrombin according to claim 12 wherein the buffer comprises 20 mM citrate, and has a pH 6.5.

14. A process for preparing thrombin according to claim 12 further comprising treatment of the diluted thrombin preparation to remove unwanted insoluble material, said treatment is selected from the group consisting of centrifugation, filtration and centrifugation, and filtration.

15. A process for preparing thrombin according to claim 12 further comprising further processing to yield a thrombin of higher purity, wherein the further processing comprises chromatographic purification and wherein the thrombin of higher purity is eluted using a suitable buffer of pH 6.0 to 7.0.

16. A process for preparing thrombin according to claim 15 further comprising a viral inactivation step, prior to the chromatographic purification.

17. A heat-treated freeze-dried thrombin preparation, prepared according to the process of claim 1, wherein said preparation is free of exogenous stabilizing agents, said exogenous stabilizing agents is selected from the group consisting of protein, sugar or polyol and mixtures thereof and wherein the preparation has been heat-treated in order to inactivate any virus contaminants.

18. A heat-treated freeze-dried thrombin preparation according to claim 17, wherein the heat-treated thrombin preparation has been dry heat-treated at a temperature between 70° C. to 100° C. for up to 96 hours.

19. A heat-treated freeze-dried thrombin preparation according to claim 17; wherein the heat-treated thrombin preparation has been heat-treated at 80° C. for at least 72 hours.

20. A heat-treated freeze-dried thrombin preparation according to claim 17, wherein the preparation is freeze-dried employing a two-stage freezing procedure, comprising a primary drying at a shelf temperature of −20° C. to −30° C. and a secondary drying at a shelf temperature of +15° C. to +30° C.

21. A heat-treated freeze-dried thrombin preparation according to claim 17 which has been prepared from a liquid formulation comprising 10 mM–30 mM citrate.

22. A heat-treated freeze-dried thrombin preparation according to claim 21 wherein the liquid formulation further comprises 100 mM–250 mM sodium chloride.

23. A heat-treated freeze-dried thrombin preparation according to claim 21, wherein the liquid formulation is buffered to between pH 6.4–6.6 with 20 mM MES or 20–40 mM gluconic acid.

* * * * *

UNITED STATES PATENT AND TRADEMARK OFFICE
CERTIFICATE OF CORRECTION

PATENT NO. : 5,907,032

DATED : 25 May 1999

INVENTOR(S) : Ian Randle MacGregor; John Charles Hardy; Olive Drummond

It is certified that error appears in the above-identified patent and that said Letters Patent is hereby corrected as shown below:

Title page, item [75]:
Under paragraph entitled "Inventors" correct to read
--Ian Randle MacGregor; John Charles Hardy, both of Edinburgh; Olive Drummond, Fife, all of United Kingdom--

Title page, item [30]:
Under paragraph entitled "Foreign Application Priority Data" correct to read
--Feb 24, 1995 [GB]  United Kingdom........................9503750.3--

Column 11, Claim 19 correct "A heat-treated freeze-dried thrombin preparation according to claim 17; . . ." to read "A heat-treated freeze-dried thrombin preparation according to claim 17, . . ."--

Signed and Sealed this

Twenty-second Day of February, 2000

Attest:

Q. TODD DICKINSON

*Attesting Officer*        *Commissioner of Patents and Trademarks*